United States Patent [19]

Cassata

[11] 4,137,266

[45] Jan. 30, 1979

[54] PROCESS FOR TOLUENE DIAMINE RECOVERY

[75] Inventor: John R. Cassata, Beaverton, Oreg.

[73] Assignee: Olin Corporation, New Haven, Conn.

[21] Appl. No.: 833,416

[22] Filed: Sep. 15, 1977

Related U.S. Application Data

[63] Continuation-in-part of Ser. No. 726,852, Sep. 27, 1976, abandoned.

[51] Int. Cl.$^2$ ...................... C07C 85/20; C07C 85/26
[52] U.S. Cl. ............................... 260/578; 260/465 H; 260/582
[58] Field of Search .................... 260/582, 578, 465 H

[56] References Cited

U.S. PATENT DOCUMENTS

| | | | |
|---|---|---|---|
| 3,128,310 | 4/1964 | Koch | 260/582 |
| 3,210,395 | 10/1965 | McDougall | 260/453 |
| 3,331,876 | 7/1967 | Van Horn et al. | 260/582 |
| 4,032,574 | 6/1977 | Keshi et al. | 260/570 D |

OTHER PUBLICATIONS

Hackh's Chemical Dictionary, p. 26 (1969).
Sidgwick's Organic Chemistry of Nitrogen, p. 236, (1966).

*Primary Examiner*—Winston A. Douglas
*Assistant Examiner*—John Doll
*Attorney, Agent, or Firm*—F. A. Iskander; Robert J. Feltovic; Thomas P. O'Day

[57] ABSTRACT

Toluene diamine is obtained by hydrolyzing the toluene diisocyanate distillation residue in the presence of aqueous ammonia.

11 Claims, No Drawings

PROCESS FOR TOLUENE DIAMINE RECOVERY

This application is a continuation-in-part of co-pending application Ser. No. 726,852, filed Sept. 27, 1976, now abandoned.

This invention relates to an improved process for the recovery of toluene diamine from the distillation residue which is obtained in the production of toluene diisocyanate.

Toluene diisocyanate is produced on a large commercial scale by a process wherein toluene diamine is reacted with excess phosgene usually in the presence of an organic solvent medium. An illustrative process is described in U.S. Pat. No. 3,287,387. Along with toluene diisocyanate, the phosgenation product mixture usually comprises unreacted phosgene, solvent, hydrogen chloride by-product, and a relatively substantial proportion of side reaction products in the form of residual and high boiling materials.

Recovery of most of the toluene diisocyanate from this mixture is achieved by distillation which is usually carried out in two or more steps wherein the low boiling components are removed first before recovering the toluene diisocyanate. A considerable amount of distillation residue is left behind.

Under certain conditions, toluene diamine values can be recovered from this residue by hydrolysis. So recovered, the toluene diamine can then be used for making more toluene diisocyanate. Thus U.S. Pat. No. 3,128,310 discloses a method for toluene diamine recovery wherein the residue is heated to a temperature of about 160°–250° C. in the presence of water and preferably a small proportion of alkali metal hydroxide catalyst. Additionally, U.S. Pat. No. 3,331,876 discloses an improvement in this hydrolysis technique. To increase the yield of toluene diamine, the patent calls for effecting the hydrolysis at a temperature of 260°–350° C. and in the presence of a relatively high proportion of alkali metal hydroxide.

Further in this art, U.S. Pat. No. 3,210,395 discloses the concept of bubbling anhydrous ammonia into a toluene diisocyanate distillation residue containing solvent. This treatment, which is carried out at elevated temperatures, e.g., 100°–300° C. or higher, is said to bring about precipitation of the tarry by-products contained in the residue.

Now an improvement has been found in the art of hydrolyzing the toluene diisocyanate distillation residue to recover toluene diamine therefrom. According to the invention, the improvement resides in the use of an aqueous solution of ammonia as the hydrolysis catalyst. Two economically and practically important advantages are realized by using such a catalyst as compared with the prior art use of alkali metal hydroxides. First, unlike alkali metal hydroxides the recovery of which is either impractical or entails costly operations, aqueous ammonia can be easily recovered by simple distillation. So recovered, it can be recycled for use again and again.

Another advantage connected with the use of ammonia is very important from an environmental standpoint. Specifically, after recovery of toluene diamine from the hydrolysis product, a residue is left which contains varying amounts of residual, unrecoverable toluene diamine. Since the diamine is known to be a carcinogen, it is imperative from an environmental standpoint that all traces of it in the residue waste be destroyed. To this end, the residue must be burned off or incinerated. Such a residue, when sodium hydroxide is used as the hydrolysis catalyst, will contain this alkali metal in the form of NaOH and NaCl, the latter being a by-product formed during hydrolysis as a result of a side reaction between caustic and hydrolyzable chlorides which are present in the original toluene diisocyanate distillation residue. Since it is well known that alkali metals cannot be burned off easily and in fact attack the refractory lining of incinerators, a problem arises in connection with incinerating the final residue when an alkali metal (e.g., NaOH and/or NaCl) is present therein. By contrast, when aqueous ammonia is used as the hydrolysis catalyst, its presence in the final residue will be in the form of ammonium chloride. This, unlike NaOH and NaCl, can be easily incinerated without any damage to the incinerator lining.

The process of the invention can be carried out batchwise or on a continuation basis. Generally continuous operation is preferred as it is more rapidly adapted to commercial practice in connection with the continuous production of toluene diisocyanate.

The process applies to the treatment of any residue which results from the distillation of the product of phosgenating toluene diamine. As commonly used in the commercial production of toluene diisocyanate, the toluene diamine is typically made up of a mixture of 2,4- and 2,6-isomers and may in addition contain traces of ortho-toluene diamine. The distillation residue is usually dark, viscous liquid which is substantially free of solvent. Along with varying traces of phosgene and by-product hydrochloric acid, it normally has a residual content of toluene diisocyanate ranging from about 15 to about 70% by weight, the balance being made up of high boiling and tarry by-products of the phosgenation reaction.

The hydrolysis catalyst which is employed according to the invention is an aqueous solution of ammonia. Such a solution, which may be prepared in advance or formed in-situ, can be provided for example by mixing water with ammonia or with a suitable ammonium salt such as ammonium carbonate, ammonium bicarbonate or the like. Thus it is to be understood that the terms "aqueous ammonia" and "aqueous solution of ammonia", as used in the specification and claims herein, are clearly intended to mean and encompass an aqueous medium containing ammonia, which medium is provided by any such techniques. In accordance with the preferred embodiments of the invention, the aqueous solution of ammonia is provided from a mixture of water with ammonia or ammonium carbonate. The use of ammonium carbonate is particularly preferred.

Generally, the concentration of the solution can be varied over a wide range so long as it is effective in catalyzing the hydrolysis. Illustratively, the concentration of ammonia in the aqueous solution may range from about 0.2 to about 25, and preferably about 0.5–15, percent by weight. In accordance with the most preferred embodiments of the invention, an ammonia concentration of about 1–12 in the aqueous solution is employed.

The aqueous solution of ammonia is employed in any proportion which is effective in catalyzing the hydrolysis of the toluene diisocyanate distillation residue. Illustratively, such a proportion is used as to provide an equivalent amount of anhydrous ammonia ranging from about 1 to about 50, and preferably about 3–25, parts per every 100 parts by weight of the residue.

Except for the use of aqueous ammonia as the catalyst, the hydrolysis of the toluene diisocyanate distillation residue is carried out using prior art methods. Such methods are described, for example, in U.S. Pat. No. 3,331,876, issued July 18, 1976, and U.S. Pat. No. 3,128,310, issued Apr. 7, 1964, the entire disclosures of which are incorporated herein by reference. For example, the toluene diisocyanate distillation residue may be placed in a reactor or autoclave. Hydrolysis is then effected by adding and mixing in the requisite amount of aqueous ammonia, and heating the mixture to elevated temperatures in order to bring about the hydrolysis reaction. If desired, particularly where a concentrated solution of aqueous ammonia is used, additional amounts of water or steam may be added, but then the consequent dilution should be kept in mind so that the desired or prescribed concentration of ammonia can be maintained.

As indicated, the hydrolysis is effected at elevated temperatures. In accordance with the prior art, such temperatures may range from about 150° to about 350° C. For optimum results, a temperature of about 200°-320° C., and more preferably about 220°-300° C., is employed. It is also preferable to maintain the reactor at elevated or super-atmospheric pressure, e.g., about 50-3,000 psig and more preferably about 100-2,400, during the effectuation of the hydrolysis reaction, which may take anywhere from a few minutes to several hours to be completed. The reaction product mixture is then subjected first to atmospheric distillation in order to remove the aqueous ammonia and then to low-pressure or vacuum distillation to recover the toluene diamine. The residue left from the second distillation can be relatively easily disposed of by incineration. Conveniently, the aqueous ammonia that is removed may be recycled for use again.

It is to be noted that where the TDI distillation residue is provided as a solid, usually in large chunks, or where such large chunks are formed in the course of the hydrolysis, it may be necessary to subdivide it. This may be achieved by means of appropriate grinding or shear-mixing equipment.

In accordance with one preferred embodiment of the invention, the hydrolysis of the toluene diisocyanate distillation residue is carried out step-wise using the following procedure. First, it is mixed with the aqueous ammonia at moderate temperatures, i.e., about 30°-55° C. This treatment effects the transformation of the residue into an inert, granular solid that is easy to handle or transport either as a slurry in the aqueous medium, or upon separation from the aqueous medium and subsequent drying, as a granulated, nontoxic, and free-flowing material. This granular material, either in the form of a slurry in the aqueous medium or as a dry product is then subjected to hydrolysis by heating to the elevated temperatures specified above in the presence of aqueous ammonia. Thus pursuant to this preferred embodiment, the process of the invention comprises the steps of (a) transforming the residue into a granular material by mixing it with the aqueous ammonia at a temperature of about 25°-65° C., and preferably about 30°-55° C., and then, (b) hydrolyzing the granular material at a temperature of about 150°-350° C., preferably about 200°-320° C., and more preferably about 220°-300° C., in the presence of aqueous ammonia.

In both of the above steps, the concentration of the aqueous ammonia solution is the same as specified hereinabove; and in the first step, i.e., that of transforming the residue into a granular material by treatment with ammonia at moderate temperatures, any suitable proportion of the ammonia solution may be used which is effective in achieving the objectives of that step. Illustratively, such a proportion is used as to provide the equivalent of about 5-500, and preferably about 10-200, parts of anhydrous ammonia per every 100 parts by weight of the toluene diisocyanate distillation residue.

An important practical advantage is realized by practicing the above-described step-wise technique in effecting the hydrolysis according to the invention. Specifically, by transforming the residue into a granular, inert material, the need for using grinding or shearing equipment is eliminated. Furthermore, any toxicity or pollution problems connected with handling the residue prior to hydrolysis are obviated by the transformation of the residue into a non-toxic, inert material. Still further, inasmuch as it has been found that ammonia is better suited for use in deactivating the residue than alkali metal hydroxides, its use in the above-described two-step process is particularly advantageous.

The toluene diamine prepared by the process of the invention can be converted to toluene diisocyanate by reaction with phosgene. In this regard, the process of the invention is particularly suited for use in connection with the commercial-scale production of toluene diisocyanate by the phosgenation technique. Thus after toluene diisocyanate is recovered from the phosgenation product by distillation, the process of the invention can be used to recover toluene diamine from the distillation residue, which toluene diamine can then be recycled to the phosgenation reactor for conversion to the corresponding isocyanate.

The following examples are provided to illustrate the invention. The toluene diisocyanate distillation residue which is referred to and used throughout the examples was a solvent-free material obtained by a conventional method, as described for example in U.S. Pat. No. 3,287,387 to Denton et al, for the commercial production of toluene diisocyanate. More specifically, this method involves (a) reacting, at about 120° C., excess phosgene with a solution of toluene diamine (mixture of 2,4- and 2,6-isomers) in monochlorobenzene solvent, (b) removing the monochlorobenzene, unreacted phosgene and by-product HCl from the phosgenation product, and (c) further distilling the remaining product to recover overhead pure toluene diisocyanate. The residue from this distillation is used in the examples.

Further in the examples, all parts and percentages are by weight unless otherwise specified.

EXAMPLE I

Into a 2-liter, high pressure autoclave, equipped with a mechanical agitator, heating mantle and thermocouple, there were placed 200 grams of toluene diisocyanate distillation residue which had been dried to a solid by vacuum distillation and finely divided to less than 100 mesh particle size. Also placed in the autoclave were 793.6 grams of water to which had been added 6.4 grams of ammonia. The contents of the autoclave were kept under agitation while being heated gradually up to a temperature of 240° C. It was noted that the hydrolysis reaction was substantially completed when the temperature reached 198° C. At the end of one hour at 240° C., the heating mantle was de-energized and the reaction product mixture was allowed to cool to room temperature. It was then subjected to atmospheric distillation to remove the water and ammonia followed by vacuum distillation to removed the toluene diamine that was formed. The identity of the toluene diamine was confirmed by vapor phase chromatography which also revealed no presence of any ortho-isomers. Yield of toluene diamine was calculated at 0.660 gram per every gram of dry residue initially placed in the autoclave.

Comparison 1

The identical procedure of Example 1 was followed except that in lieu of the aqueous ammonia, aqueous caustic was used, specifically 8 grams of NaOH and 792 grams of water. It was noted that the hydrolysis reaction was substantially completed when the temperature inside the autoclave reached 225° C.

Toluene diamine yield was calculated at 0.654 gram per every gram of residue initially placed in the autoclave. The content of ortho-isomer was 0.037%, based on the total weight of pure toluene diamine obtained.

Comparison 2

Again the identical procedure of Example 1 was followed except that here water was used alone (800 grams) in the absence of ammonia or other basic material. The reaction was completed when the temperature inside the autoclave reached 215° C. Toluene diamine yield was 0.644 gram per gram of residue and the ortho-isomer content in the toluene diamine obtained was 0.123%.

EXAMPLE II

Into a 2-liter, high pressure autoclave, equipped with a mechanical agitator, heating mantle and thermocouple, there were placed 50 grams of toluene diisocyanate distillation residue which had been deactivated by heating to 50° C. with 8% aqueous $NH_3$ solution and dried. Also placed in the autoclave were 247.2 grams of water to which had been added 52.8 grams of ammonium carbonate. The contents of the autoclave were kept under agitation while being heated gradually up to a temperature of 240° C. At the end of one hour at 240° C., the heating mantle was de-energized and the reaction product mixture was allowed to cool to room temperature. It was then subjected to atmospheric distillation to remove the water and ammonia followed by vacuum distillation to remove the toluene diamine that was formed. Yield of toluene diamine was calculated at 0.600 gram per every gram of deactivated residue initially placed in the autoclave. The content of ortho-isomer was 0.065%, based on the total weight of pure toluene diamine obtained.

What is claimed is:

1. In a process for the preparation of toluene diamine which comprises hydrolyzing, at a temperature of about 150°–350° C., a substantially solvent-free residue obtained from the distillation of the product of phosgenating toluene diamine, the improvement characterized by first transforming said residue into a granular material by heating it, in the presence of aqueous ammonia, to a temperature of about 25° to about 65° C., and then effecting the hydrolysis of said residue by heating it, in the presence of an aqueous solution of ammonia, to a temperature of about 150° to about 350° C.

2. The process of claim 1 wherein said aqueous solution of ammonia is obtained by mixing water with ammonia or ammonium carbonate.

3. The process of claim 2 wherein said ammonium carbonate is employed.

4. The process of claim 1 wherein the hydrolysis temperature ranges from about 200° to about 320° C.

5. The process of claim 4 wherein the hydrolysis is effected at super-atmospheric pressure.

6. The process of claim 5 wherein said aqueous solution of ammonia has a concentration of about 0.2 to about 25 percent by weight.

7. The process of claim 6 wherein said aqueous solution of ammonia is used in a proportion such as to provide the equivalent of about 1–50 parts of anhydrous ammonia per every 100 parts by weight of said residue.

8. The process of claim 7 wherein said pressure is about 100–2400 psig.

9. The process of claim 8 wherein said temperature is about 220°–300° C. and said aqueous ammonia concentration is about 0.5–15 percent by weight.

10. The process of claim 9 which includes the preparatory step of transforming said residue into a granular material by heating it, in the presence of aqueous ammonia, to a temperature of about 30°–55° C.

11. The process of claim 10 wherein said aqueous solution of ammonia is obtained by mixing water with ammonium carbonate.

* * * * *